United States Patent [19]
Saboory

[11] Patent Number: 5,584,078
[45] Date of Patent: Dec. 17, 1996

[54] DETACHABLE/DISPOSABLE FACE SHIELD FOR SURGICAL MASK

[76] Inventor: Majid Saboory, 2536 Dupont Ave. S., #204, Minneapolis, Minn. 55405

[21] Appl. No.: 340,547

[22] Filed: Nov. 16, 1994

[51] Int. Cl.⁶ .......................... A62B 18/00; A62B 18/02; A61F 9/04
[52] U.S. Cl. ........................................ 2/427; 2/9; 128/857
[58] Field of Search .................................. 2/427, 9, 206; 128/206.19, 201.17, 206.23, 857, 858, 863

[56] References Cited

U.S. PATENT DOCUMENTS

| | | |
|---|---|---|
| 2,669,717 | 2/1954 | Diggs ...................................... 2/427 X |
| 3,298,031 | 1/1967 | Morgan ................................... 2/427 X |
| 4,414,693 | 11/1983 | Brody ......................................... 2/435 |
| 4,825,878 | 5/1989 | Kuntz et al. . |
| 4,852,185 | 8/1989 | Olson . |
| 4,944,294 | 7/1990 | Borek, Jr. . |
| 4,966,140 | 10/1990 | Herzberg . |
| 5,020,533 | 6/1991 | Hubbard et al. . |
| 5,067,174 | 11/1991 | Ritchey et al. . |
| 5,107,547 | 4/1992 | Scheu . |
| 5,144,695 | 9/1992 | Schweizer .......................... 2/209.13 X |
| 5,303,423 | 4/1994 | Gazzara et al. . |
| 5,406,944 | 4/1995 | Gazzara ............................. 128/857 X |

FOREIGN PATENT DOCUMENTS 0625344  11/1994  European Pat. Off. ................... 2/427

Primary Examiner—Peter Nerbun
Attorney, Agent, or Firm—Palmatier, Sjoquist, Helget & Voigt, P.A.

[57] ABSTRACT

The present invention relates to a light-weight disposable/detachable face shield for the protection of the eyes and face of wearers from accidental exposure to infectious, hazardous and undesirable substances. It is of particular interest in the protection of health care workers and professionals and laboratory personnel from accidental exposure to body fluids from infected patients. The shield is attachable to an unmodified, standard surgical mask. The shield comprises a fluid-impervious, transparent panel for protecting the eyes and face of the wearer, and a clip, attached to the panel, which reversibly engages the mask, thereby securely and reversibly holding the face shield to the mask.

18 Claims, 4 Drawing Sheets

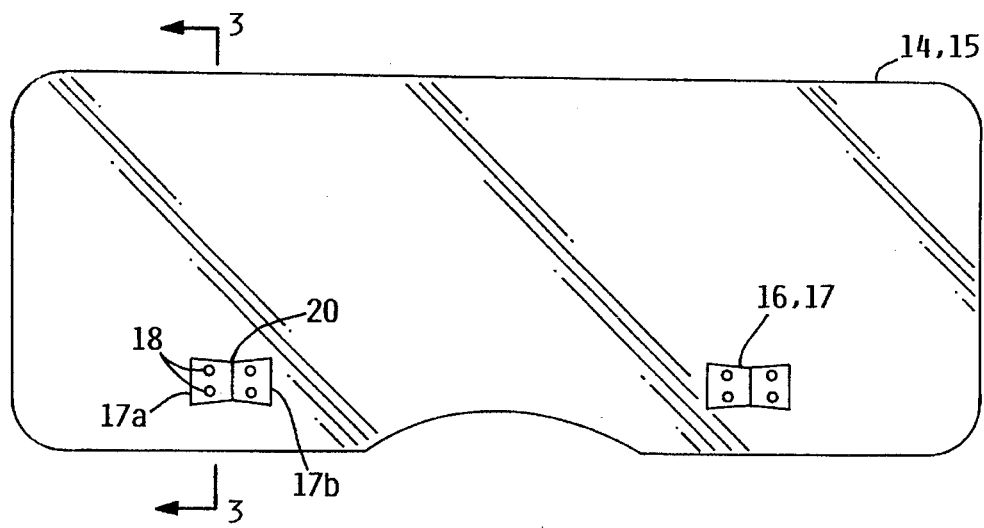
FIG. 2
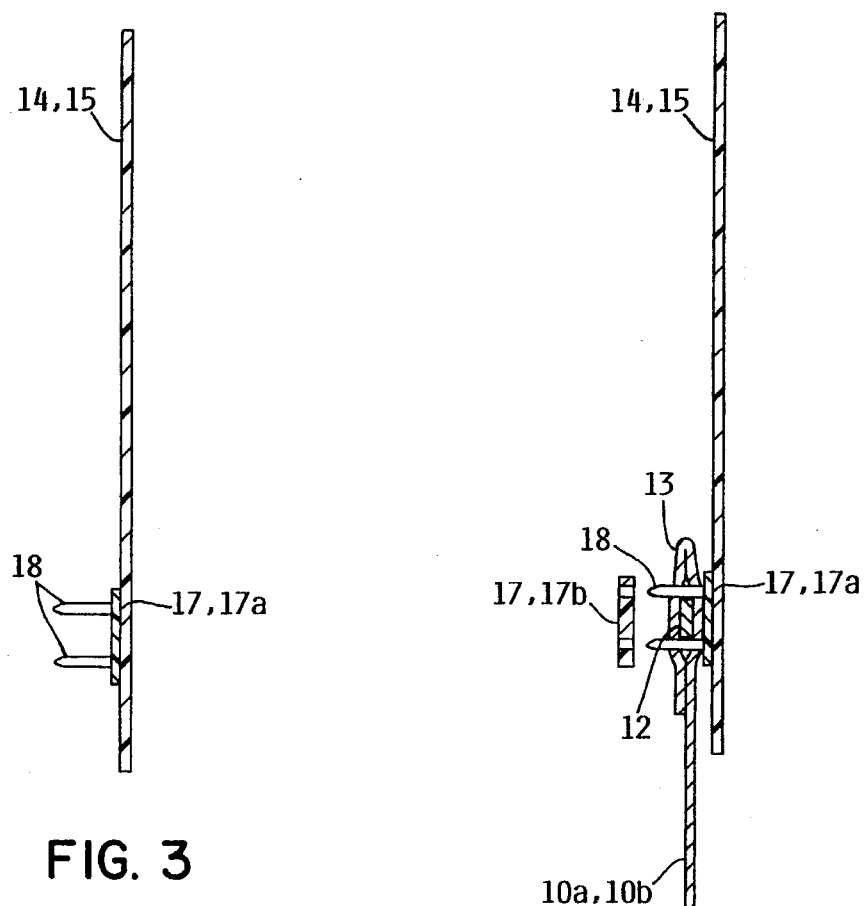
FIG. 3
FIG. 4

000
DETACHABLE/DISPOSABLE FACE SHIELD FOR SURGICAL MASK

BACKGROUND OF THE INVENTION

The present invention relates to a detachable/disposable face shield for the protection of the eyes and face of wearers from accidental exposure to infectious, hazardous and undesirable substances. More particulate, the invention relates to anti-infection shields for the protection of health care workers and professionals and laboratory personnel from accidental exposure to infectious and/or hazardous fluids and particulate materials.

Health care workers have long recognized that caring for patients with certain infectious diseases poses risk of contracting such diseases. For example, many cases have been reported of accidental transmission of Hepatitis B from patients to persons involved in their care. More recently, the life threatening epidemic of Acquired Immune Deficiency Syndrome (AIDS) caused by Human Immuno Deficiency Virus (HIV) has aroused great concern. Although the bulk of cases of patients to health care worker cross infection have resulted from accidental needle sticks, medical office, hospital, surgical, dental and laboratory personnel are now required to use extreme care in the handling of all patients and body fluids as potentially infected with HIV and other pathogens. Particular attention has been directed to the risk to surgeons and operating personnel of infection through splashing or splattering of blood or other body fluids onto open wounds, into mouths or into the eyes of such personnel during the performance of surgical procedures.

The United States Centers for Disease Control of the U.S. Department of Health and Human Services, has issued a comprehensive series of recommendations for the prevention of all HIV transmission in health care settings and such recommendations are applicable to the risk of exposure to all infected body fluids. These recommendations show an increasing concern for protection of the eyes (particular conjunctiva) if aerosolization or splashing of blood or other fluids is likely to occur. Thus, according to the Centers for Disease Control, eye shields should be worn by medical personnel and laboratory workers to prevent blood and other body fluids from splattering into the eyes. An effective eye shield must protect the eyes no matter which direction the wearer faces. Ordinary eyeglasses are not sufficient protection.

Although a number of protective face shields are known in the medical and dental professions, such shields either do not have a means for attaching to a standard, unmodified surgical mask, or the surgical mask is permanently affixed to the face shield.

These shields are undesirable, because a mask is generally required and if the mask becomes contaminated with infectious fluids, both the mask and the shield must be thrown away.

There is a need for a disposable, detachable face shield for attachment to a standard unmodified surgical mask, so that the shield may be removed from a contaminated mask and the mask disposed of while reusing the shield by attachment to a fresh mask. The shield must be attachable to a standard surgical mask without any modifications to the mask, in order to take advantage of existing surgical masks and not require the worker to purchase a special mask in order to use the shield.

SUMMARY OF THE INVENTION

The present invention relates to a light-weight disposable/detachable face shield for the protection of the eyes and face of wearers from accidental exposure to infectious, hazardous and undesirable substances. It is of particular interest in the protection of health care workers and professionals and laboratory personnel from accidental exposure to body fluids from infected patients. The shield is attachable to an unmodified, standard surgical mask. The shield comprises a fluid-impervious, transparent panel for protecting the eyes and face of the wearer, and a clip, attached to the panel, which reversibly engages the mask, thereby securely and reversibly holding the face shield to the mask.

A principle object and advantage of the present invention is that it provides a detachable/disposable face shield for attachment to an unmodified standard surgical mask. The shield may be attached to a standard mask which is easily and readily available without any special modifications. Furthermore the shield may be easily detached from the mask when the mask becomes contaminated.

It is further an object and advantage of the invention to provide the face shield with clips integrally molded thereto for attaching to the upper margin of the standard surgical mask.

It is a further object and advantage of the invention that the shield and clips may be cheaply and easily manufactured as a single unit from transparent plastic.

It is a further object and advantage of the invention that the clips, while quickly attachable to the mask, securely hold the shield to the mask without significant movement.

A further object and advantage of the invention is that the clip consists of two parts which are connected together by a thin living hinge, so that the parts may be quickly and easily separated by the wearer for attaching the clips to the mask.

A further object and advantage of the present invention is that the shield is made of a plastic that has been coated with an anti-fog agent to prevent the wearer's breath from fogging up the shield when the mask is worn.

BRIEF DESCRIPTION OF THE DRAWINGS

FIG. 2 is a rear elevational view of the face shield of the present invention.

FIG. 3 is a cross-sectional view of the face shield of the present invention along the lines 3—3 in FIG. 2.

FIG. 4 is a cross-sectional view similar to FIG. 3, additionally showing the attachment of the face shield of the present invention to a surgical mask.

DETAILED DESCRIPTION OF THE PREFERRED EMBODIMENTS

Figure 1A:
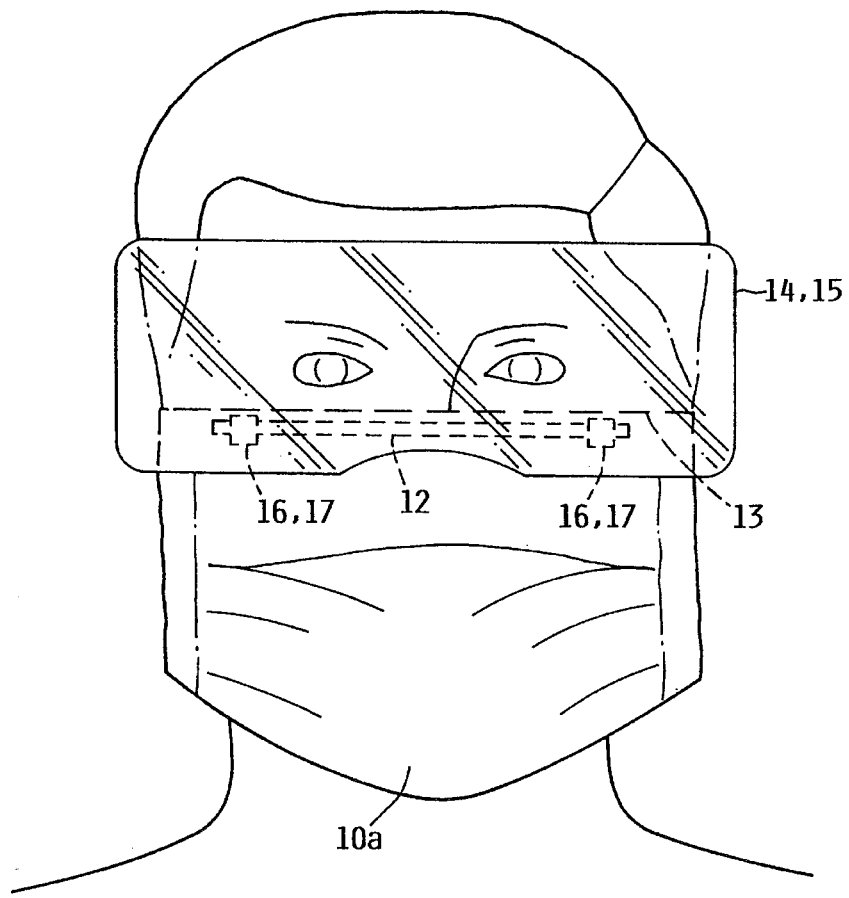
FIG. 1A is a perspective view of the face shield of the present invention attached to a rectangular surgical mask on the face of a worker.
Figure 1B:
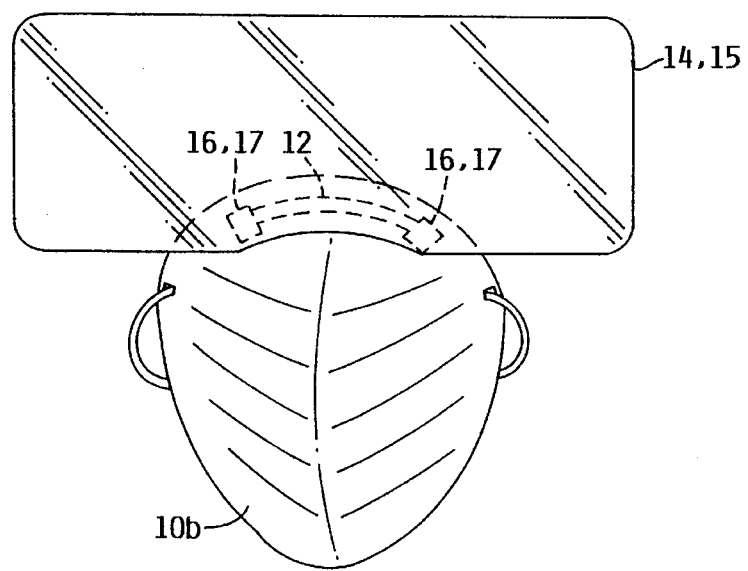
FIG. 1B is a perspective view of the face shield of the present invention attached to an oval surgical mask.

The detachable/disposable face shield of the present invention is shown in the drawings by reference numeral 14.

As can be seen in the drawings, the face shield 14 attaches to an unmodified, standard surgical mask 10a, 10b. The mask 10a, 10b may have an embedded pliable metal insert 12 along the upper margin 13 of the mask 10a, 10b.

The face shield 14 comprises a fluid-impervious, transparent panel 15 for protecting the eyes and face of the wearer, and a means 16 for reversibly attaching the panel 15 to the mask 10a, 10b by attachment to the embedded pliable metal insert 12.

FIG. 2 further illustrates that the means for attaching 16 further comprises a clip 17. As seen in FIG. 4, in one embodiment the clip 17 engages the embedded pliable metal insert 12.

FIGS. 2, 3, and 4 disclose that in the first embodiment the clip 17 further comprises a first tab 17a attached to the panel 15. The first tab 17a has a plurality of prongs 18 for penetrating the fabric of the mask 10a, 10b about the metal insert 12. The clip 17 also comprises a second tab 17b which engages the prongs 18 and mask 10a, 10b about the pliable metal insert 12. As can be seen, the second tab 17b will press the mask 10a,10b against the first tab 17a, thereby securely and reversibly holding the face shield 14 to the mask 10a, 10b.

In the first embodiment, the second tab 17b is attached to the first tab 17a and is detachable from the first tab 17a. An equivalent arrangement (not shown), however, would be for the second tab 17b to remain attached to the first tab 17a to mount the shield 14 to the mask 10a, 10b. In such an arrangement, the second tab 17b is attached to the first tab 17a by a hinge, so that the second tab 17b may fold downwardly over the upper margin 13 of the mask 10a, 10b and thereby engage the prongs 18.

In the first embodiment, the second tab 17b is attached to the first tab 17a by a living hinge 20. In order to detach the second tab 17b from the first tab 17a, the wearer grasps the shield 14 and twists the second tab 17b back and forth until the hinge 20 is broken. The wearer then presses the detached second tab 17b against the prongs 18 and mask 10a, 10b as shown in FIG. 4, thus attaching the shield 14 to the mask 10a, 10b.

In order to re-use the shield with a clean mask, the wearer simply pulls the second tab 17b away from its engagement with the prongs 18, lifts the mask 10a, 10b off the prongs 18, and inserts the prongs 18 into a fresh mask, then re-applies the second tab 17b.

Figure 5A:
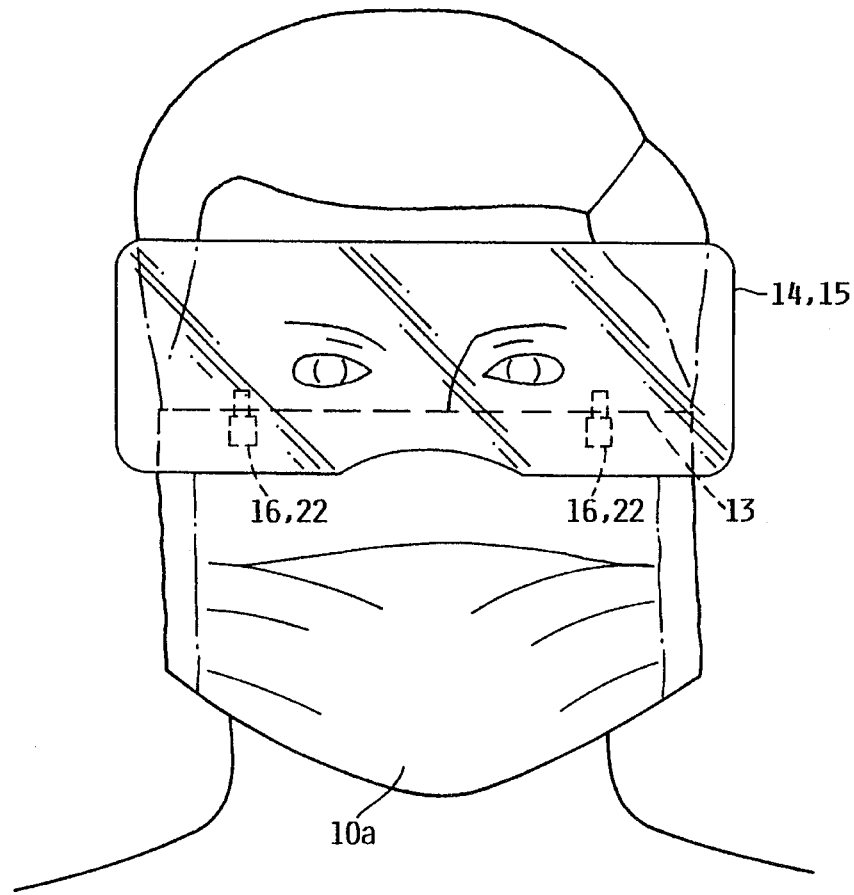
FIG. 5A is a perspective view of a second embodiment of the face shield of the present invention attached to a rectangular surgical mask on the face of a worker.
Figure 5B:
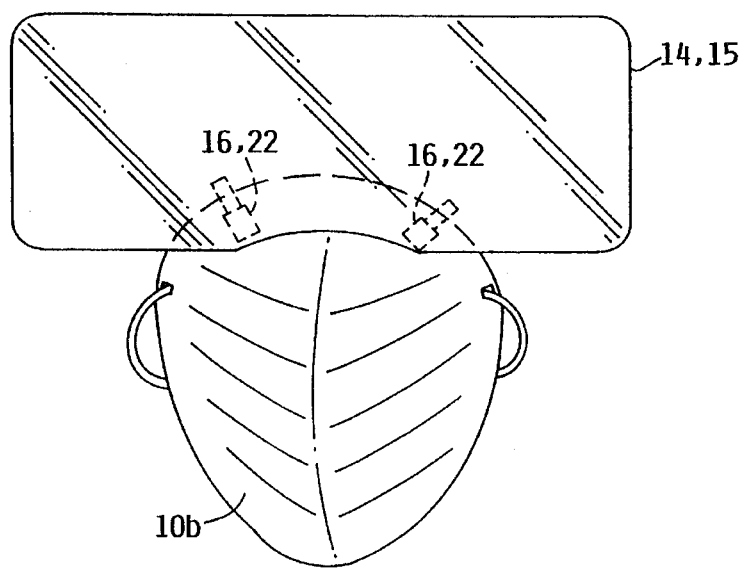
FIG. 5B is a perspective view of a second embodiment of the face shield of the present invention attached to an oval surgical mask.
Figure 6:
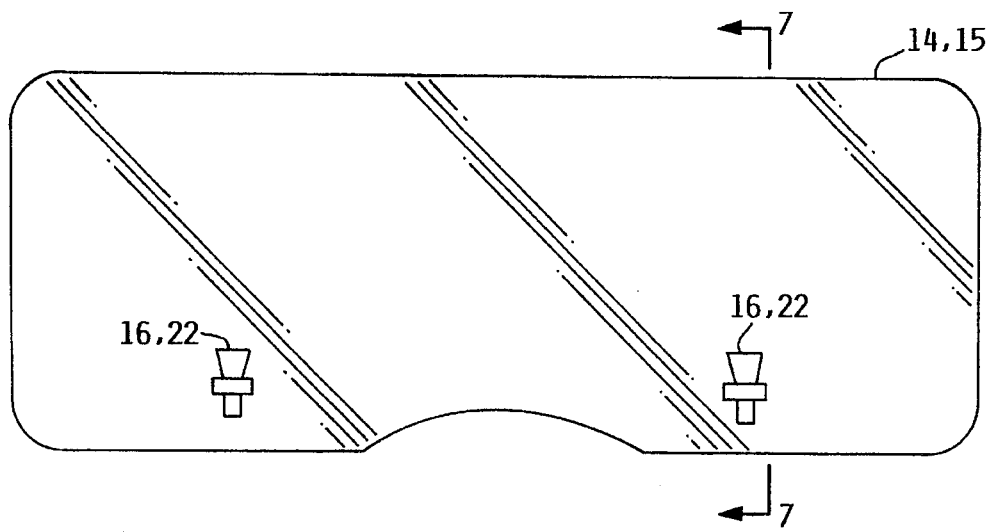
FIG. 6 is a rear elevational view of a second embodiment of the face shield of the present invention.
Figure 7:
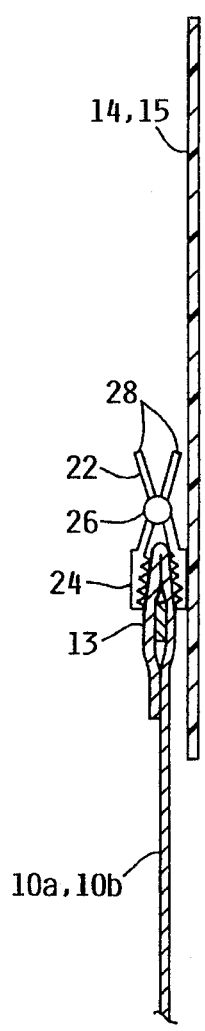
FIG. 7 is a cross-sectional view of a second embodiment of the present invention along the lines 7—7 in FIG. 6.

In a second embodiment, shown in FIG. 5, 5A, 5B, 6 and 7, the means for attaching 16 further comprises an "alligator" or "clothespin" type clip 22, attached to the panel 15. The clip 22 comprises a pair of jaws 24 which are biased together by a spring 26. The clip also has a pair of handles 28 which when pressed together by the wearer, cause the jaws 24 to open. The shield 14 is then attached to the mask 10a, 10b by placing the open jaws 24 over the upper margin 13 of the mask 10a, 10b and releasing the handles 28, causing the jaws 24 to clamp onto the upper margin 13. In this manner, the shield 15 may be attached to any surgical mask 10a, 10b.

The shield 14 may optionally be made of plastic that has been coated with an anti-fogging agent to prevent the wearer's breath from fogging up the shield when the mask is worn.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A detachable/disposable face shield adapted for attachment to an unmodified, standard surgical mask having an upper margin, and a pliable metal insert along the upper margin said face shield comprising:

a fluid-impervious, clear, transparent panel for protecting the eyes and face of health care workers and professionals and laboratory personnel from accidental exposure to infectious and/or hazardous fluids and particulate materials, and means for detachably attaching the panel to the unmodified standard surgical mask, and the attaching means further comprises a clip which is adapted to engage the pliable metal insert of the mask, wherein the clip further comprises a first tab attached to the panel and having a plurality of prongs for penetrating the mask fabric about the pliable metal insert and a second tab for engaging the prongs and mask fabric, thereby securely and reversibly holding the face shield to the mask.

2. The detachable/disposable face shield of claim 1, wherein the second tab is attached to the first tab.

3. The detachable/disposable face shield of claim 2, wherein the second tab is attached to the first tab by a hinge.

4. The detachable/disposable face shield of claim 2, wherein the second tab is detachable from the first tab.

5. The detachable/disposable face shield of claim 4, wherein the second tab is attached to the first tab by a living hinge which may be broken by twisting the second tab.

6. The detachable/disposable face shield of claim 1, wherein the panel is made of plastic that has been coated with an anti-fogging agent to prevent the wearer's breath from fogging up the shield when the mask is worn.

7. A detachable/disposable face shield and mask, comprising:

an unmodified, standard surgical mask having an embedded pliable metal insert along the upper margin of the mask, a fluid-impervious, transparent panel for protecting the eyes and face of the wearer, and a clip, attached to the panel, wherein the clip reversibly engages the pliable metal insert of the mask, thereby securely and reversibly holding the face shield to the mask, wherein the clip further comprises a first tab attached to the panel and having a plurality of prongs for penetrating the mask fabric about the pliable metal insert and a second tab for engaging the prongs and mask fabric, thereby securely and reversibly holding the face shield to the mask.

8. The detachable/disposable face shield of claim 7, wherein the second tab is attached to the first tab.

9. The detachable/disposable face shield of claim 8, wherein the second tab is attached to the first tab by a hinge.

10. The detachable/disposable face shield of claim 8, wherein the second tab is detachable from the first tab.

11. The detachable/disposable face shield of claim 10, wherein the second tab is attached to the first tab by a living hinge which may be broken by twisting the second tab.

12. The detachable/disposable face shield of claim 7, wherein the panel is made of plastic that has been coated with an anti-fogging agent to prevent the wearer's breath from fogging up the shield when the mask is worn.

13. A detachable/disposable face shield for attachment to an unmodified, standard surgical mask of the type having an embedded pliable metal insert along the upper margin of the mask, comprising:

a fluid-impervious, transparent panel for protecting the eyes and face of the wearer, and a clip, attached to the panel, wherein the clip is adapted to reversibly engage the pliable metal insert of the mask, thereby securely and reversibly holding the face shield to the mask, wherein the clip further comprises a first tab attached to the panel and having a plurality of prongs for penetrating the mask fabric about the pliable metal insert and a second tab for engaging the prongs and mask fabric, thereby securely and reversibly holding the face shield to the mask.

14. The detachable/disposable face shield of claim 13, wherein the second tab is attached to the first tab.

15. The detachable disposable face shield of claim 13, wherein the second tab is attached to the first tab by a hinge.

16. The detachable/disposable face shield of claim 14, wherein the second tab is detachable from the first tab.

17. The detachable/disposable face shield of claim 16, wherein the second tab is attached to the first tab by a living hinge which may be broken by twisting the second tab.

18. The detachable/disposable face shield of claim 13, wherein the panel is made of plastic that has been coated with an anti-fogging agent to prevent the wearer's breath from fogging up the shield when the mask is worn.

* * * * *